United States Patent [19]
Campbell et al.

[11] 3,974,170
[45] Aug. 10, 1976

[54] PREPARATION OF 2-MERCAPTOAZOLES

[75] Inventors: Robert Henry Campbell, Akron; Alfred Bay Sullivan, Wadsworth, both of Ohio

[73] Assignee: Monsanto Company, St. Louis, Mo.

[22] Filed: Aug. 26, 1974

[21] Appl. No.: 500,461

[52] U.S. Cl. .......................... 260/306; 260/247.1 L; 260/293.57; 260/294.8 C; 260/302 S; 260/306.7 R; 260/307 R; 260/307 F; 260/309; 260/309.2
[51] Int. Cl.² ..................................... C07D 277/72
[58] Field of Search .......... 260/306, 306.5, 241.1 L, 260/293.57, 294.8 C

[56] References Cited
UNITED STATES PATENTS

| | | |
|---|---|---|
| 2,018,813 | 10/1935 | Schubert et al. .................. 260/306.5 |
| 2,051,806 | 8/1936 | Allen .................................. 260/306 |
| 2,259,356 | 10/1941 | Smith ................................. 260/306 |
| 2,509,453 | 5/1950 | Russell ............................... 260/306 |
| 3,759,931 | 9/1973 | Brown et al. ...................... 260/306 |
| 3,773,779 | 11/1973 | Jager et al. ....................... 260/306 |

*Primary Examiner*—R. J. Gallagher

[57] ABSTRACT

A process is disclosed which comprises reacting hydrogen sulfide with azolesulfonates and sulfinates to give 2-mercaptoazoles. One embodiment of the invention describes removal of oxidized forms of 2-mercaptobenzothiazole including benzothiazole-2-sulfonates from effluent by treatment with hydrogen sulfide.

21 Claims, 2 Drawing Figures

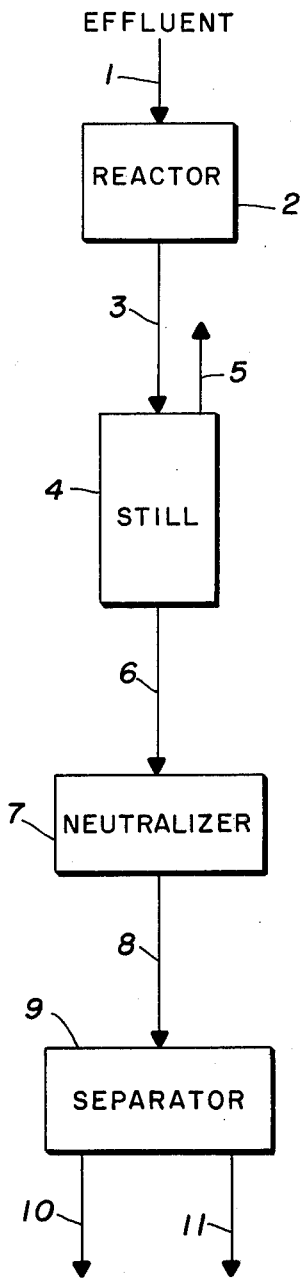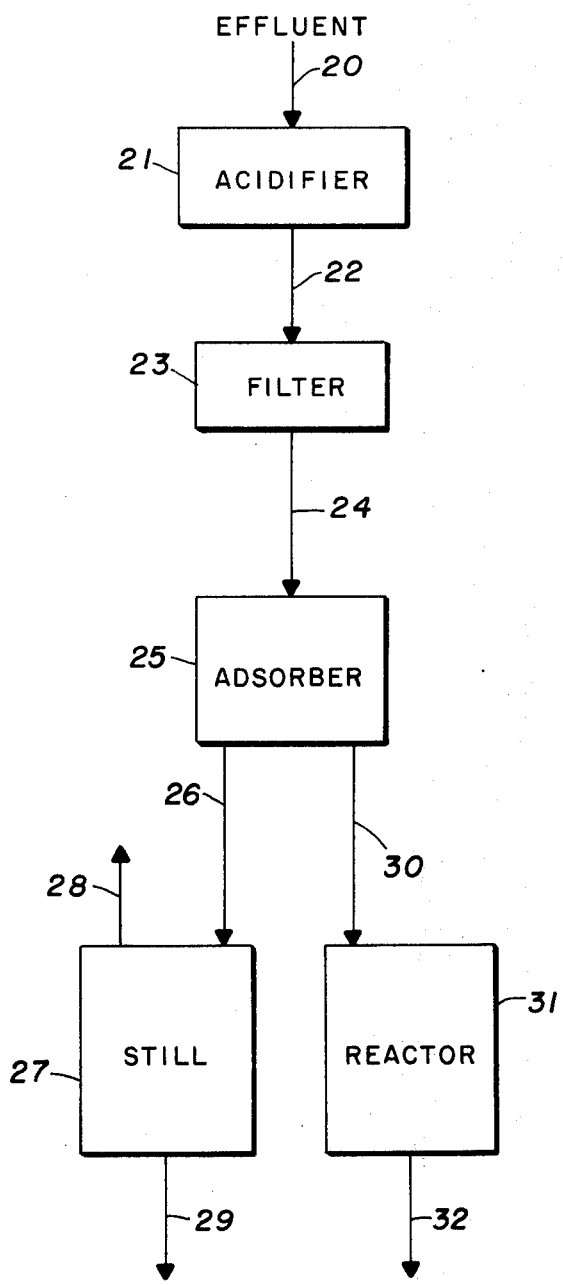
FIG. 1.                    FIG. 2.

PREPARATION OF 2-MERCAPTOAZOLES

This invention relates to a process of preparing mercaptoazoles by reacting hydrogen sulfide or hydrogen sulfide precursor with azole sulfonic acid, azole sulfinic acid or salts thereof and particularly, to a process for treating effluent containing azole sulfonates and sulfinates and recovering mercaptoazole. Processes concerning the preparation of 2-mercaptoazoles are classified in Patent Office Class 260, subclass 306.

BACKGROUND OF THE INVENTION

Benzothiazole disulfide and benzothiazole sulfenamides are used extensively as accelerators in the vulcanization of rubber. One process for the manufacture of benzothiazole disulfide comprises the oxidation of sodium 2-mercaptobenzothiazole to bis(2-benzathiazolyl) disulfide and one process for the manufacture of benzothiazolyl sulfenamides comprises the oxidation of an amine salt of 2-mercaptobenzothiazole to benzothiazole sulfenamide. After the products are recovered, effluent from both processes contain oxidized forms of 2-mercaptobenzothiazole including significant quantities of benzothiazole sulfonates which oxidized products represent an economic loss based on conversion of starting materials and which pose ecological problems when the effluent is discharged into a river or tributary thereof.

The reaction of hydrogen sulfide with sulfonates has not been extensively studied but the studies which have been reported indicate that the yields are too low for practical interest. Only compounds containing an activated sulfur group, such as, in 2,4-dinitrobenzene-sulfonic acid or potassium anthraquinone-2-sulfonate appear to undergo significant reaction. Surprisingly, now it has been found that hydrogen sulfide reacts essentially quantitatively with azole-sulfonates and azole-sulfinates to give the corresponding 2-mercaptoazole. Application of this novel reaction provides a means by which benzothiazole sulfonates may be removed from effluent and 2-mercaptobenzothiazole or its salts recovered and recycled for conversion to additional disulfide or sulfenamide. Thus, this invention provides a means for purifying effluent streams while recovering valuable by-products.

SUMMARY OF THE INVENTION

The broad invention upon which other embodiments of the invention are based is the discovery that hydrogen sulfide or hydrogen sulfide precursor reacts with azole-2-sulfonate or azole-2-sulfinate to give the corresponding 2-mercaptoazole or salts thereof. The reaction is represented by the equation

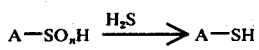

in which $n$ is 2 or 3 and A is a 2-azolyl radical. The reaction proceeds under both acid and basic conditions. The hydrogen atom may be replaced with salt cation, it is understood that equilibrium mixtures of hydrogen ion and salt cation coexist with the quantity of each being a function of pH. The nature of the salt cation is unimportant.

The 2-mercaptoazole product has a divalent sulfur atom. One valence of the sulfur is satisfied by a 2-azolyl radical while the other valence of the sulfur is satisfied to either a salt cation or to a hydrogen atom depending upon the pH. Acidification of a solution comprising a salt of 2-mercaptoazole gives the corresponding 2-mercaptoazole. Solubility of 2-mercaptoazoles in water varies with temperature and pH. Consequently, when 2-mercaptoazoles are soluble, particularly when present in low concentrations, for example, at 0.5% or less, it is preferable to recover them either by solvent extraction or by adsorption techniques. When the mercaptoazoles are insoluble and present in slurry form, they may be conveniently recovered by filtration or hydroclassification.

The reaction takes place under both acid and basic conditions and at relatively low temperatures. The reaction proceeds slowly at room temperature requiring long times to achieve substantial conversion of reactants, however, by elevating the temperature, the rate of reaction is increased sufficiently to achieve essentially complete conversion within reasonable times. For example, adequate reaction rates are realized from 40° to 130°C or above with a preferred temperature range being between 45°–120°C with a range of 50°–110°C being more preferred. Acid conditions also appear to promote the rate of reaction. Preferably, the reaction is carried out in aqueous solution. The reaction rate is dependent upon reactant concentration with an excess of either reactant promoting reaction, however, satisfactory rates are obtained even with concentrations of less than 0.01%. One of the advantages of treating effluent containing benzothiazole-2-sulfonates with hydrogen sulfide is that the reaction proceeds to completion even when the benzothiazole-2-sulfonates are present at extremely low concentrations. Although the reaction is ordinarily conducted at atmospheric pressure, it may be carried out at superatmospheric pressure, if desired, which superatmospheric conditions may be advantageous when a gaseous reactant such as hydrogen sulfide is used since high pressure increases its concentration.

The process of the invention is applicable to all azole-2-sulfonates and particularly is applicable to benzothiazole-2-sulfonates. The process also applies to lower oxidized forms of 2-thioazoles, such as, azole-2-sulfinates. However, since azole-2sulfinates tend to disproportionate to give azole-2-sulfonates and in order to avoid repetition, the process will be described in terms of azole-2-sulfonate with it being understood that the process is equally applicable to azole-2-sulfinates. Reaction of hydrogen sulfide or hydrogen sulfide precursor with azole-2-sulfonate give compounds of the formula A—S—R in which A is 2-azolyl and R is hydrogen or salt cation. Suitable 2-azolyl radicals are 2-thiazolyl, 2-oxazolyl, 2-imidazolyl and said radicals substituted on the vicinal carbon atoms, 2-thiazolyl radicals are preferred.

Illustrative azole-2-sulfonates and azole-2-sulfinates suitable as intermediates for the process of the invention are characterized by the formula A—SO$_n$—R in which A and R are the same as above and $n$ is 2 or 3. Illustrative examples of benzoazole-2-sulfonic acids satisfactory for use in the process of this invention are described in U.S. Pat. No. 2,018,813, the disclosure of which is incorporated herein by reference.

Azole radicals designated as A above are characterized by the formula

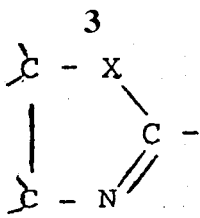

wherein the unsatisfied valences on the vicinal carbon atoms are attached to hydrogen, lower alkyl, benzyl, acetyl, carboalkoxy and phenyl or together with the carbon atoms form an alicyclic ring or an ortho arylene ring, or two of the unsatisfied valences are joined to form a double bond. The ortho arylene ring may be sustituted by lower alkyl, halo, nitro, hydroxy, carboalkoxy, acetyl, lower alkoxy and phenyl radicals, and X is S, N or O. Lower alkyl means alkyl radicals containing 1–5 carbon atoms.

Specific examples of azole radicals are 2-thiazolyl, 2-thiazolinyl, 2-oxazolyl, 2-oxazolinyl, 2-benzothiazolyl, 2-benzoxazolyl, 2-benzimidazolyl, 2-naphthathiazolyl, 2-dihydrobenzothiazolyl, 2-(4,5,6,7-tetrahydrobenzothiazolyl), 2-(4-methylthiazolyl), 2-(4-methylthiazolyl), 2-(4-methyloxazolyl), 2-(4-ethylthiazolyl), 2-(4-ethyloxazolyl), 2-(4-n-propylthiazolyl), 2-(4-n-propyloxazolyl), 2-(4-n-butylthiazolyl), 2-(4-n-butyloxazolyl), 2-(4,5-dimethylthiazolyl), 2-(4,5-dimethyloxazolyl), 2-(4,5-diethylthiazolyl), 2-(4,5-diethyloxazolyl), 2-(4,5-di-n-propylthiazolyl), 2-(4,5-di-n-propyloxazolyl), 2-(4,5-di-n-butylthiazolyl), 2-(4,5-di-n-butyloxazolyl), 2-(4,5-diphenylthiazolyl), 2-(4,5-diphenyloxazolyl), 2-(4-phenyl-5-methylthiazolyl), 2-(4-phenyl-5-methyloxazolyl), 2-(5-acetyl-4-methylthiazolyl), 2-(5-carbomethoxy-4methylthiazolyl), 2-(5-carbethoxy-4-methylthiazolyl), 2-(5-carbethoxythiazolyl), 2-(5-carbamoyl-4-methylthiazolyl), 2-(5-carbanilino-4-methylthiazolyl), 2-(4-ethylbenzothiazolyl), 2-(4-ethylbenzoxazolyl), 2-(5-chlorobenzothiazolyl), 2-(5-chlorobenzoxazolyl), 2-(6-ethoxybenzothiazolyl), 2-(6-ethoxybenzoxazolyl), 2-(4-phenylbenzothiazolyl), 2-(4-phenylbenzoxazolyl), 2-(5-carbethoxybenzothiazolyl), 2-(5-carbethoxybenzoxazolyl), 2-(6-nitrobenzothiazolyl), 2-(6-nitrobenzoxazolyl), 2-(4-methylbenzothiazolyl), 2-(4-methylbenzoxazolyl), 2-(5-ethylbenzothiazolyl), 2-(5-ethylbenzoxazolyl), 2-(6-tert-butylbenzothiazolyl), 2-(6-tert-butylbenzoxazolyl), 2-(4,6-dimethylbenzothiazolyl), 2-(4,6-dimethylbenzoxazolyl), 2-(5,6-diethylbenzothiazolyl), 2-(5,6-diethylbenzoxazolyl), 2-(7-methylbenzothiazolyl), 2-(7-methylbenzoxazolyl), 2-(6-octylbenzothiazolyl), 2-(6-octylbenzoxazolyl), 2-(4-methylthiazolinyl), 2-(5-methylthiazolinyl), 2-(4,4-dimethylthiazolinyl), 2-(5,5-dimethylthiazolinyl), 2-(4-ethylthiazoliny), 2-(4butylthiazolinyl), 2-(4-methyl-5-butylthiazolinyl), 2-(4-phenylthiazolinyl), 2-(4-benzylthiazolinyl), 2-[4-(2-hydroxyethyl)-thiazolinyl], 2-(4-chloro-5-methylthiazolinyl), 2-(4-chloro-5-ethylthiazolinyl), 2-(4-hydroxythiazolinyl), 2-(4-methoxythiazolinyl), 2-(4-aminothiazolinyl), 2-(5-chlorothiazolinyl), 2-(5,5-dimethyloxazolinyl), 2-(4,5-dimethyloxazolinyl), 2-(4-ethyloxazolinyl), 2-(5-ethyloxazolinyl), 2-(4-methyloxazolinyl), 2-(4,4-dimethyloxazolinyl), 2-(4-phenyloxazolinyl), 2-(4-methoxyoxazolinyl), 2-(4-butyloxazolinyl), 2-(5-amyloxazolinyl) and the corresponding imidazolyl radicals. Of the azole radicals, thiazolyl radicals and especially benzothiazolyl are preferred.

The term "azole-2-sulfonate" as used herein and in the claims means a compound of the formula A—SO$_3$—R in which A and R are the same as described before, which definition includes both the azole-2-sulfonic acid and salts thereof.

The term "hydrogen sulfide precursor" as used herein and in the claims means a compound which under acid conditions gives hydrogen sulfide, it being understood that the liberation of hydrogen sulfide under acid conditions is merely a property of a hydrogen sulfide precursor and that any of the processes described herein are not limited in any way to acid conditions since hydrogen sulfide precursors react and are effective for the purposes of this invention under basic or acid conditions. Typical hydrogen sulfide precursors are sodium hydrosulfide, potassium hydrosulfide, lithium hydrosulfide, sodium monosulfide, potassium monosulfide, lithium sulfide, sodium tetrasulfide, potassium disulfide, potassium trisulfide, potassium tetrasulfide, ammonium polysulfide and thioacetamide. The alkali metal hydrosulfides and monosulfides are preferred.

The term "salt cation" as used herein and in the claims means any positively charged ion which cation may be a positively charged atom or group of atoms. The nature of the salt cation is of no consequence being solely dependent upon the nature of the ion species available in the solution. Both inorganic and organic cations are satisfactory. Inorganic cations are generally metal atoms, for example, alkali earth metals and alkali metals. Salt cations which are water soluble are preferred with cations derived from alkali metals comprising a preferred subgroup with sodium and potassium being preferred species. Examples of organic salt cations are cations derived from pyridine and amines.

Satisfactory amine cations are represented by the formula $R_{(3-m)}$—N—$H_{(m+1)}$$^+$ in which $m$ is zero, 1, 2 or 3 and R is an organic radical attached to nitrogen which cation is formed by the addition of a portion to ammonia or an organic amine. Primary and secondary aliphatic amines comprise an important subclass, particularly primary and secondary lower alkyl amines, for example, isopropylamine, diisopropylamine and tert-butylamine. Another subclass comprises cycloalkylamines, such as cyclohexylamine and dicyclohexylmine and still another subclass comprises heterocyclicamines, such as piperidine, morpholine and hexahydro-(1H)-azepine.

Examples of compounds which may be prepared by the process of the invention are 2-mercaptobenzothiazole, 2-mercaptothiazole, 2-mercaptothiazoline, 2-mercaptoxazole, 2-mercaptoxazoline, 2-mercaptoimidazole, 2-mercaptobenzimidazole, 2-mercapto-6-ethoxy-benzothiazole, 2-mercapto-4-methylbenzothiazole, 2-mercapto-4-methyl-6-chlorobenzothiazole, 2-mercapto-6-chlorobenzothiazole, 2-mercapto-6-nitrobenzothiazole, and the corresponding salts of said 2-mercaptoazoles.

The process of the invention is applicable for conversion of azole-2-sulfonates in an effluent to the corresponding 2-mercaptoazole or salts thereof. The process is especially applicable for the beneficiation of an aqueous effluent containing oxidized forms of 2-mercaptobenzothiazole including benzothiazole-2-sulfonate. For example, one embodiment of the invention comprises treating an effluent containing benzothiazole-2-sulfonate with hydrogen sulfide or hydrogen sulfide precursor and thereby converting the benzothiazole-2- sulfonate to 2-mercaptobenzothiazole or salts thereof. Similarly, treating an effluent containing benzothiazole-2-sulfinic acid or salts thereof with hydrogen sulfide converts the benzothiazole-2-sulfinate to 2-mercaptobenzothiazole and salts thereof. The reaction is illustrated by the equation:

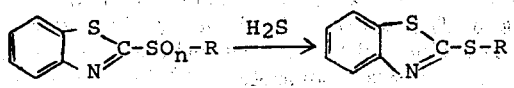

in which $n$ is two or three and R is hydrogen or salt cation.

The hydrogen sulfide reaction affords a convenient means of removing contaminants, which heretofore were not readily removed, such as benzothiazole-2-sulfonic acid and its salts from effluent streams by converting said contaminants to 2-mercaptobenzothiazole or salts thereof which conversion products are readily separated from the effluent and if desired may be recycled for conversion into either benzothiazole sulfenamide or bis(benzothiazolyl)disulfide.

Typically, effluent from a commercial sulfenamide plant contains up to 0.5 mmoles of sodium benzothiazole-2-sulfinate and up to 1 mmole of sodium benzothiazole-2-sulfonate per 100 grams of effluent. However, the process of the invention is applicable to solutions of higher or lower concentrations. Generally, the concentration of contaminants is within the range of 0.05–0.3 mmoles of sodium benzothiazole-2-sulfinate and 0.1–0.7 mmoles of sodium benzothiazole-2-sulfonate. An effluent treated by the process of the invention gives waste streams containing 5% or less of the original amounts of the aforesaid contaminants.

A better understanding of the process of treating effluent with hydrogen sulfide may be obtained by referring to the Drawings and the Detailed Description thereof.

DESCRIPTION OF THE DRAWINGS

FIG. 1 is a flow sheet of a process for treating an effluent containing benzothiazole-2-sulfonate with hydrogen sulfide.

FIG. 2 is a flow sheet of a process for removing benzothiazole-2-sulfonate contaminants from an effluent in which said contaminants are concentrated prior to hydrogen sulfide treatment.

DETAILED DESCRIPTION

Referring to FIG. 1, an effluent 1 of a benzothiazole-2-sulfenamide plant is charged to reactor 2 equipped with a gas sparging means, temperature control means and pressure control means. Hydrogen sulfide is sparged into reactor 2 until essentially all the benzothiazole-2-sulfonates and sulfinates are converted to 2-mercaptobenzothiazole or salts thereof. The hydrogen sulfide treated effluent 3 passes to still 4. After addition of caustic, the material is refluxed and amine is recovered in distillate 5. Amine-depleted effluent 6 passes to neutrilizer 7 and mineral acid is added to adjust the pH to about 6–7. Hydrogen sulfide evolved by the acid addition is vented through an outlet not shown and recycled back to reactor 2. Neutralized effluent 8 passes to separator 9. In separator 9, 2-mercaptobenzothiazole and salts thereof are separated from the bulk of the effluent and waste stream 10 containing a reduced level of benzothiazole-2-sulfonates and sulfinates is discharged to the sewer. Stream 11 containing 2-mercaptobenzothiazole and salts thereof leaves separator 9 which compounds are recovered or preferably stream 11 is recycled back to the sulfenamide plant to convert the compounds to additional sulfenamide.

Separation of by-product and waste streams in separator 9 may be effected by various means. For example, the separator may merely comprise the steps of acidification to precipitate 2-mercaptobenzothiazole followed by filtration to recover the precipitated 2-mercaptobenzothiazole. A preferred means for separating 2-mercaptobenzothiazole comprises a two-phase liquid separation in which the aqueous effluent, preferably at pH 7 or below, is contacted with an immiscible organic solvent, for example, toluene, into which the 2-mercaptobenzothiazole is absorbed. Generally, two-phase liquid separations are effected by passing the aqueous phase down a column while simultaneously passing the organic phase upward. The aqueous stream is discharged to the sewer and the organic stream goes to a system for recovering 2-mercaptobenzothiazole or is recycled.

Whenever an effluent is amine free or if it is undesirable to recover amine, the system illustrated by FIG. 1 may be modified by by-passing still 4 and neutralizer 5 and feeding hydrogen sulfide treated effluent 3 directly into separator 9.

Referring to FIG. 2, effluent 20 of a benzothiazole-2-sulfenamide plant is charged to acidifier 21 equipped with temperature control means and sirring means. Mineral acid, for example, sulfuric acid, is fed into acidifier 21 until the pH is about 5. The acid converts any benzothiazole-2-sulfinic acid or salts thereof to benzothiazole, precipitates 2-mercaptobenzothiazole from any salts of 2-mercaptobenzothiazole present and forms alkali metal sulfate and amine sulfate. Salts of benzothiazole-2-sulfonic acid are converted to benzothiazole-2-sulfonic acid. Slurry 22 passed to filter 23 in which 2-mercaptobenzothiazole is recovered. Filtrate 24 goes to adsorber 25 which comprises a bed of solid particles capable of adsorbing benzothiazole-2-sulfonic acid. Benzothiazole, residual quantities of 2-mercaptobenzothiazole and benzothiazole-2-sulfonic acid are adsorbed on the solid particles of the bed. The adsorbent solid particles may be anion exchange resin or preferably activated carbon. Stream 26 depleted of benzothiazole-2-sulfonic acid exits adsorber 25 which stream may optionally be discharged into the sewer or, as shown, is fed into still 27 to recover amine. After addition of caustic to still 27, the material is refluxed and amine recovered in distillate 28. An improved waste stream 29 containing substantially reduced levels of amine and benzothiazole-2-sulfonic acid, benzothiazole-2-sulfinic acid and salts thereof is discharged.

Adsorber 25 is eluted with caustic solution which converts the adsorber benzothiazole-2-sulfonic acid to the sodium salt. Stream 30 comprising a solution of sodium benzothiazole-2-sulfonate is fed to reactor 31. Hydrogen sulfide is sparged in reactor 31 until essentially all of the sodium benzothiazole-2-sulfonate is converted to 2-mercaptobenzothiazole or sodium 2-mercaptobenzothiazole. Optionally, in place of sparging hydrogen sulfide, a hydrogen sulfide precursor, for example, sodium hydrosulfide, may be charged to reactor 31. Stream 32 containing 2-mercaptobenzothiazole and sodium salt thereof discharges from reactor 31 which compounds are recovered, or preferably; stream 32 is sent back to the sulfenamide plant wherein the compounds are converted into sulfenamide.

One advantage of this embodiment is that the adsorbent bed concentrates the benzothiazole-2-sulfonic acid and upon elution gives a substantially enriched solution of sodium benzothiazole-2-sulfonate thereby providing a reduced volume of solution which subsequently is treated with hydrogen sulfide.

Analysis and identification of components of effluent solutions at intermediate stages in the process and waste and by-product streams are made by liquid chromatographic separation using an anion exchange column with an eluting aqueous solvent adjusted for pH and ionic strength to achieve maximum separation of all components and by using an ultraviolet detection system with an internal standard calibrated with authenic samples of each component. The anion exchange column is one meter in length and operated at ambient temperature. Eluent flow is controlled at approximately 1.6 ml/min. at 2000 psi. The eluent is an aqueous buffer solution comprising 0.01 molar $KH_2PO_4$ or boric acid adjusted to pH 7.5 and 0.08 molar $KNO_3$. The internal standard solution comprises 5.0 milligrams of p-nitrophenol per milliliter of 0.1 normal NaOH.

PREFERRED EMBODIMENTS

The following illustrates an embodiment of the invention following the process shown in FIG. 2. A 45.359 kg quantity of effluent 20 (twice filtered filtrate from tert-butyl benzothiazole-2-sulfenamide plant) is charged to acidifier 21 and acidified to pH 4.5–5.5 by addition of 1950 g. of 25% $H_2SO_4$ at 60°–70°C. During acidification, temperatures exceeding 70°C and pH below 4 are avoided to prevent hydrolysis of benzothiazole-2-sulfonic acid to 2-hydroxybenzothiazole. Acidification converts tert-butylamine to di(tert-butylamine)sulfate, sodium 2-mercaptobenzothiazole to 2-mercaptobenzothiazole, sodium benzothiazole-2-sulfonate to benzothiazole-2-sulfonic acid and sodium benzothiazole-2-sulfinate to benzothiazole-2-sulfinic acid which acid rapidly hydrolyzes to benzothiazole. In this example, the acidified effluent 22 goes directly to adsorber 25 without filtration because the quantity of solid 2-mercaptobenzothiazole present in this instance is captured in the adsorber making filtration unnecessary. The acidified effluent passes through adsorber 25 which comprises a column containing more than 200 grams (preferably about 360 grams) of granular activated carbon (Pittsburgh Type CAL, 12 × 40 mesh). Essentially all of the 2-mercaptobenzothiazole, benzothiazole and benzothiazole-2-sulfonic acid are adsorbed in the column. When operating the process continuously, stream 26 leaving adsorber 25 is monitored and when the concentration of benzothiazole-2-sulfonic acid increases significantly indicating that the capacity of the bed is about to be exceeded, acidified effluent 22 is diverted to an alternate adsorber column while the original column is being reactivated as described below. Stream 26 depleted of benzothiazole-2-sulfonic acid with its major organic component now being di(tert-butylamine)sulfate passes from the column to still 27 in which tert-butylamine is recovered. Adsorber 25 is washed with 1665 g. of water (about 4 column volumes) to remove residual quantities of di(tert-butylamine)sulfate retained on the carbon which wash water also goes to still 27 for amine recovery. After distillation, the bulk of stream 26 is emptied from the bottom of the still as waste stream 29 which stream contains substantially reduced quantities of amine and benzothiazole-2-sulfonate. Adsorber 25 is washed with 1696 g. of 3% NaOH solution at 40°–65°C and then washed with 1626 g. of water. The combined caustic and water washes gives solution 30 having a pH of 11.0–11.5 which solution is charged to reactor 31. Solution 30 comprises 3.4% 2-mercaptobenzothiazole (as the sodium salt), 1.8% benzothiazole, 0.01% sodium 2-hydroxybenzothiazole, 1.3% sodium benzothiazole-2-sulfonate and 0.4% tert-butylamine. The pH is adjusted to 8–9 by adding 204 g. of 25% $H_2SO_4$ solution. The reactor head space is purged with nitrogen to remove a small quantity of tert-butylamine vapors evolved during the acid addition. Hydrogen sulfide is sparged through the solution at 65°–70°C for 15 hours during which time the pH drops to 4.5–5.0. Residual quantities of $H_2S$ are purged from the reactor with nitrogen. 2223 g. of 25% NaOH is added to the solution giving a pH of 11.0–12.0. While maintaining the temperature of 65°–70°C, a vacuum (380 mm Hg) is applied to the reactor to strip out the remaining tert-butylamine. The step of stripping residual amine from the solution is optional and is generally unnecessary provided the quantity of amine remaining is acceptable. Solution 32 containing 4.4% sodium 2-mercaptobenzothiazole, 1.8% benzothiazole, 0.01% sodium hydroxy-2-benzothiazole, 0.06% sodium benzothiazole-2-sulfonate and 0.01% tert-butylamine is discharged from the reactor and recycled to the sulfenamide plant. The hydrogen sulfide treatment results in a significant reduction in sodium benzothiazole-2-sulfonate and an essentially proportional increase in sodium 2-mercaptobenzothiazole.

A study is conducted of the effect of hydrogen sulfide treatment of effluent from a benzothiazole-2-sulfenamide plant. The assay of the effluent varies somewhat between samples but a representative assay (expressed in mmoles/100g; BT=2-benzothiazolyl) is 0.96 BTSNa, 0.41 BTH, 0.12 $BTSO_2Na$, 0.03 BTONa, and 0.50 $BTSO_3Na$. The amount of amine present in each sample also varies. A sample of effluent is charged into a suitable container positioned in a constant temperature bath at 100°C. Hydrogen sulfide (in substantial excess) is slowly bubbled through the sample. No effort to control pH is made. Generally, the initial pH of the sample is above 11 and is about 7 after the hydrogen sulfide addition. At various time intervals, a portion of the sample is withdrawn, acidified with acetic acid (a quantity of alcohol is added to keep the BTSH in solution) and analyzed for 2-mercaptobenzothiazole. The analysis shows that the time required for complete conversion of both the $BTSO_2$— and $BTSO_3$— to BTSH varies from about one to four hours but usually is about 2 hours. Adjusting the initial pH of the sample to about 8–9 by adding mineral acid prior to hydrogen sulfide addition reduces the time to achieve complete conversion and lowers the hydrogen sulfide consumption.

Two experiments are conducted following the above procedure but using synthetic samples containing only $BTSH_3^-$. One synthetic sample is prepared by combining 53.7 parts of benzothiazole-2-sulfonic acid, 2650 parts of 0.0944 normal NaOH and 313 parts of tert-butylamine and diluting with sufficient water to give a $BTSO_3^-$ concentration of about 1 mmole/100g of solution. The other synthetic sample is the same except the NaOH solution is omitted. In each experiment, analyses indicate that in about 6 hours, over 90 percent of the benzothiazole-2-sulfonate is converted to 2-mercaptobenzothiazole.

An autoclave heated to about 90°C is charged with a portion of an effluent containing about 0.4 mmoles of sodium benzothiazole-2-sulfonate per liter. The autoclave is pressurized to about 40 psi with hydrogen sulfide. Samples are withdrawn from time to time and analyzed for benzothiazole-2-sulfonate. The analyses indicate that in less than 1 hour, essentially all of the benzothiazole-2-sulfonate is converted to 2-mercaptobenzothiazole.

A study is made of the effect of pH on the reaction rate in the following manner. A buffer solution is prepared by dissolving 3.1 parts of boric acid in 80 volumes of water, the pH is adjusted to the desired value by adding 6N NaOH, and sufficient water is added to make a total of 100 volumes of buffer solution. A solution containing 0.1 mole of acid per liter is prepared by dissolving 215 parts benzothiazole-2-sulfonic acid and 770 parts sodium hydrosulfide (73%) in a sufficient quantity of water to give a solution of the indicated concentration. At ambient temperature and at the high pH (greater than 12), the benzothiazole-2-sulfonic acid and sodium hydrosulfide react only very slowly and not to any appreciable extent. One volume of the reactant solution is added to 10 volumes of the buffer solution in a reactor at 100°C. Samples are withdrawn periodically and the concentration of 2-mercaptobenzothiazole is measured as described before. The half life $t_{1/2}$ of the reaction is determined by plotting the log of the change of 2-mercaptobenzothiazole concentration versus time. The time required to achieve about 95% conversion is estimated by multiplying the half-life by five. The data, shown in Table I, indicate that the rate of reaction increases as the pH decreases.

TABLE I

| pH | $t_{1/2}$, min. | 95% conversion time, hours |
|---|---|---|
| 7.0 | 56 | 4.7 |
| 8.2 | 115 | 9.6 |
| 9.1 | 190 | 15.8 |
| 10.1 | 205 | 17.1 |
| 11.3 | 240 | 20.0 |

In a similar experiment except sodium benzothiazole-2-sulfinate is reacted in a buffer solution having a pH of 8.1, complete conversion to 2-mercaptobenzothiazole is achieved in less than 23 minutes (the time the first sample is taken). This data indicate that the sulfinic species reacts one order of magnitude or more faster than the sulfonic species.

One advantage of the process of the invention is that other materials in the effluent such as benzothiazole-2-sulfenamides, -sulfonamides, and -sulfinamides are also converted and recovered as 2-mercaptobenzothiazole.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exlcusive property or privilege is claimed are defined as follows:

1. A process for preparing 2-mercaptoazoles or salts thereof which comprises reacting hydrogen sulfide or hydrogen sulfide precursor and an azole-2-sulfonate of the formula A—SO$_n$—R to obtain 2-mercaptoazoles of the formula A—S—R in which in each occurrence, A is

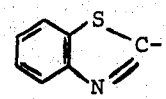

or said benzothiazolyl radical substituted on the ortho arylene ring by a member of the group consisting of lower alkyl, halo, nitro, hydroxy, carbomethoxy, carbethoxy, acetyl, lower alkoxy and phenyl, $n$ is 2 or 3 and R is hydrogen or salt cation.

2. The process of claim 1 in which the azole-2-sulfonate is in aqueous solution.

3. The process of claim 2 which comprises reacting hydrogen sulfide or hydrogen sulfide precursor selected from the group consisting of alkali metal hydrosulfide, alkali metal mono-, di-, tri- or tetrasulfide, ammonium polysulfide, and thioacetamide.

4. The process of claim 3 in which hydrogen sulfide is reacted.

5. The process of claim 4 in which

A is 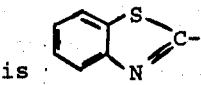

6. The process of claim 5 in which hydrogen sulfide is reacted at about 50° to about 110°C until substantially complete conversion to 2-mercaptobenzothiazole or salts thereof is effected.

7. The process of claim 6 comprising the additional steps of adjusting the pH to 7 or below and recovering 2-mercaptobenzothiazole.

8. The process of claim 2 in which there is also present azole-2-sulfinate.

9. The process of claim 2 which comprises treatment of an aqueous effluent containing oxidized forms of 2-mercaptobenzothiazole including benzothiazole-2-sulfonate which comprises reacting hydrogen sulfide or hydrogen sulfide precursor with the said oxidized forms of 2-mercaptobenzothiazole to effect conversion to 2-mercaptobenzothiazole or salts thereof, separating 2-mercaptobenzothiazole or salts thereof and discharging an improved effluent.

10. The process of claim 9 in which the benzothiazole-2-sulfonate is of the formula

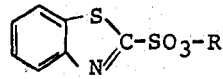

in which R is hydrogen or salt cation.

11. The process of claim 10 in which R is salt cation.

12. The process of claim 11 in which a solution of sodium benzothiazole-2-sulfonate is treated between 50°–110°C with hydrogen sulfide until substantially complete conversion to 2-mercaptobenzothiazole or salt thereof is effected.

13. The process of claim 12 in which pH of the stream is between 8–9 prior to hydrogen sulfide treatment.

14. The process of claim 13 in which the separation step comprises acidifying the treated solution and recovering 2-mercaptobenzothiazole by filtration or hydroclassification.

15. The process of claim 13 in which the separation step comprises contacting an aqueous solution containing 2-mercaptobenzothiazole or salts thereof with a water-immiscible organic solvent, extracting 2-mercaptobenzothiazole or salts thereof into the organic solvent and separating the organic phase from an aqueous waste stream.

16. The process of claim 1 which comprises acidifying an aqueous effluent containing oxidized forms of 2-mercaptobenzothiazole including benzothiazole-2-sulfonate contacting the acidified effluent with a bed of solid particles capable of adsorbing benzothiazole-2-sulfonic acid, adsorbing on the solid particles benzothiazole-2-sulfonic acid and discharging an effluent depleted of said acid, contacting the benzothiazole-2-sulfonic acid-laden solid particles with a base to convert the adsorbed acid to alkali metal benzothiazole-2-sulfonate and generating a solution of alkali metal benzothiazole-2-sulfonate, and reacting the alkali metal benzothiazole-2-sulfonate solution with hydrogen sulfide or hydrogen sulfide precursor to obtain 2-mercaptobenzothiazole or salt thereof, and separating 2-mercaptobenzothiazole or salts thereof.

17. The process of claim 16 in which the benzothiazole-2-sulfonate is of the formula

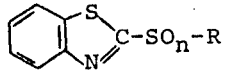

in which $n$ is 2 or 3 or mixtures thereof and R is hydrogen or salt cation.

18. The process of claim 17 in which $n$ is 3 and R is salt cation.

19. The process of claim 18 in which the bed of solid particles comprises carbon or ion-exchange resin.

20. The process of claim 19 in which the solid particles are carbon.

21. The process of claim 1 which comprises acidifying an aqueous effluent containing sodium benzothiazole-2-sulfonate, contacting the acidified effluent with a bed of carbon particles capable of adsorbing benzothiazole-2-sulfonic acid, adsorbing on the carbon particles benzothiazole-2-sulfonic acid and discharging an effluent depleted of said acid, contacting the benzothiazole-2-sulfonic acid-laden carbon particles with sodium hydroxide solution to convert the adsorbed acid to sodium benzothiazole-2-sulfonate and generating a solution of sodium benzothiazole-2-sulfonate, reacting the sodium benzothiazole-2-sulfonate solution between 50°–110°C with hydrogen sulfide, adjusting the final pH of said solution to 7 or below and recovering 2-mercaptobenzothiazole.

* * * * *